United States Patent
Heyman

(10) Patent No.: US 6,629,602 B1
(45) Date of Patent: Oct. 7, 2003

(54) CLEAR MEDICAL PACKAGING

(75) Inventor: Peter W. Heyman, Berkeley Heights, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/716,619

(22) Filed: Nov. 20, 2000

(51) Int. Cl.[7] .................................. A61B 17/06
(52) U.S. Cl. .................... 206/438; 206/366; 206/484.1
(58) Field of Search ........................... 206/438, 439, 206/363, 364, 365, 366, 484.1

(56) References Cited

U.S. PATENT DOCUMENTS

| | | | |
|---|---|---|---|
| 4,548,824 A | * 10/1985 | Mitchell et al. | ............ 206/497 |
| 4,671,943 A | * 6/1987 | Wahlquist | ................... 206/363 |
| 4,828,797 A | 5/1989 | Zwarun et al. | |
| 5,033,252 A | 7/1991 | Carter | |
| 5,052,558 A | 10/1991 | Carter | |
| 5,686,126 A | * 11/1997 | Noel et al. | ................... 206/484 |
| 5,830,547 A | 11/1998 | MacKenzie et al. | |
| 6,023,915 A | * 2/2000 | Colombo | ..................... 206/204 |
| 6,328,811 B1 | * 12/2001 | Martin et al. | ................. 134/19 |

* cited by examiner

*Primary Examiner*—Shian Luong
(74) *Attorney, Agent, or Firm*—Gregory D. DeGrazia; David M. Fortunato

(57) ABSTRACT

A medical package has a tub and a lid. The tub has a four-sided base with walls extending upwards therefrom; the walls terminate at a first flange with extends outwardly. From the first flange, four top walls extend upward and terminate at a second flange which extends outwardly. The tub is formed of a clear, ultraviolet light transmitting plastic.

The lid has a gas permeable, microfiber central portion surrounded by a clear, ultraviolet light transmitting plastic film. The film has a high shear resistance and does not produce particulate matter during an opening procedure.

14 Claims, 3 Drawing Sheets

CLEAR MEDICAL PACKAGING

FIELD OF THE INVENTION

The present invention relates to medical device packages. More particularly, the present invention relates to medical device packages having a gas permeable lid and a clear plastic tub.

BACKGROUND OF THE INVENTION

Medical devices, such as prefillable syringes and the like are frequently packaged in multi-unit packages that must be surface decontaminated prior to introduction into a controlled sterile environment where the devices are filled with medication or otherwise further manipulated prior to use, or used in a surgical procedure.

There are numerous methods used to sterilize the devices within the packages, such as gas sterilization utilizing ethylene oxide or steam sterilization. However, different methods, such as ultraviolet light sterilization, are often used for decontamination of the surfaces of the packages prior to subsequent use. It would be desirable to have a medical device package capable of use in a multitude of sterilization and decontamination techniques and yield a high level of kill of microorganisms.

A common type of package utilized in the field of medical packaging is the peel-open package. Such a package commonly comprises a thermoplastic film that is formed to a desired package shape and a lid material is then sealed to the plastic film to contain he packaged product.

The common thermoplastic film packages described above are often utilized to package individual medical devices, as the film does not provide sufficient protective characteristics for use in a multiunit package which may house delicate items. Therefore, there is a need for a multiunit package, such as a tub, that can withstand the sterilization and decontamination processes and provide a sufficient mechanical barrier to prevent damage to the items held within the package.

The lid material used is commonly a non-woven fiber arranged such that it has a microporous structure, such as Tyvek®. The microporous fiber arrangement allows gas to penetrate but has a sufficiently small pore size to block the transfer of microorganisms.

The microporous fiber arranged lid is, therefore, useful in sterilization techniques utilizing a gas, such as the aforementioned ethylene oxide and steam sterilization techniques.

The Tyvek® lid, however, does not allow the transmission of ultraviolet light that may be used as a package surface decontamination technique. Specifically, the heat seal between the lid and tub cannot be made flush with the edge of the tub flange due to processing limitations and the potential for Tyvek® tearing during peel open if an unsealed lip of Tyvek® is not available for initiation of the peeling process. Therefore, there is a region outside of the heat seal, covered by Tyvek®, which is not maintained sterile with the contents of the package. This area can be inadvertently contaminated during, manipulation of the package, as can the entire external surface of the package. However, unlike the remainder of the external surface, which can be directly exposed to ultraviolet light for decontamination, the area outside of the heat seal is blocked to the ultraviolet light by the opaque Tyvek® material on top and opaque tub material below.

Therefore, it would be desirable to utilize an ultraviolet-light transmissive plastic tub that can allow transmission of light to the underside of the heat seal area between the lid and tub to kill all microorganisms residing therein. Plastics which transmit light in the ultraviolet range typically transmit an even greater percentage of incident light in the visible (400–700 nanometer) range, resulting in a clear appearance.

An advantage of utilizing a clear plastic tub, as opposed to an opaque one is that it would allow for visual inspection of the contents of the package to determine if any of the items are damaged. This aspect offers quality control advantages to a manufacturer, as well as allow end users to ensure they are not receiving or using damaged items. Another advantage of utilizing a clear plastic tub would be the possible use of an automated visual quality system. For example, a package and its contents may be imaged and compared to a stored visual image to determine if the contents of the package are damaged. Such an automated system could provide a cost savings, as well as an increased quality control efficiency.

Alternatively, a Tyvek® lid having an ultraviolet-light transmitting plastic border that is heat sealed to a plastic tub would allow for light sterilization of the area between the lid and tub. Such a lid may be utilized with either a clear plastic tub, or with an opaque tub and allow for light to penetrate the area around the heat seal.

Another problem associated with Tyvek® lids that are known in the art, is the possibility of the Tyvek® lid shearing or tearing when peeled to open the package and thereby generating unacceptable particulate matter that may contaminate the contents of the package.

It is known in the art to coat a Tyvek® lid in an effort to reduce particulate generation, as well as prevent the lid from separating or delaminating when the heat seal strength between the lid and tub is too great. A disadvantage to this coating technique is that it has the tendency to reduce the pore size of the Tyvek® material; thereby preventing the necessary transmission of gas across the lid material or increasing the cycle time of a sterilization procedure.

It would be desirable to have a gas permeable uncoated Tyvek® lid that has a smooth continuous plastic border that is resistant to shearing and does not generate particulate matter when peeled away to access the contents.

A lid with a smooth continuous plastic border would also be desirable for use with an automated lid removal system, such as a hot knife or laser cutter that would cut the plastic border inside of the heat seal region, as an alternative to a peel-open technique.

SUMMARY OF THE INVENTION

Therefore, it is an object of the present invention to provide a medical device package which has an ultraviolet-transmissive and clear plastic tub to allow for visual inspection of the contents, as well as to allow for the transmission of microorganism killing light.

It is a further object of the present invention to provide a medical device package having a clear plastic tub that has sufficient strength characteristics to hold and protect from damage the contents of the package.

It is a further object of the present invention to provide a medical device package having a microporous, gas permeable lid that has a plastic border to minimize the creation of particulate matter when opening the package.

It is a further object of the present invention to provide a medical device package having a microporous, gas permeable lid with an ultraviolet-transmissive plastic border to facilitate the transmission of light during a decontamination process.

The present invention meets these objects by providing a medical device package having a tub having a four sided base from which four walls extend upwardly at approximately ninety degrees. The walls terminate at a first flange which extends outwardly at an angle of approximately ninety degrees from the four walls. The first flange terminates at four top walls that extend upwardly at approximately ninety degrees from the flange. The four top walls terminate at a second outwardly extending flange, which extends at an angle of approximately ninety degrees from the four top walls. The tub is formed of an ultraviolet-light transmitting plastic that is capable of withstanding exposure to gas sterilization and surface decontamination processes without degradation of the tub.

The present invention also includes a lid having a gas permeable central portion and a transparent plastic film attached to the central portion along its periphery. The plastic film overlaps the central portion when attached to assure a reliable bond of the two items. The transparent plastic film has a high shear resistance to avoid producing particulate matter when an opening force is applied. The transparent plastic film also allows transmission of ultraviolet light. These and other features of the present invention can be best understood from the following specification and drawings.

DETAILED DESCRIPTION OF THE PREFERRED EMBODIMENT

Figure 1:
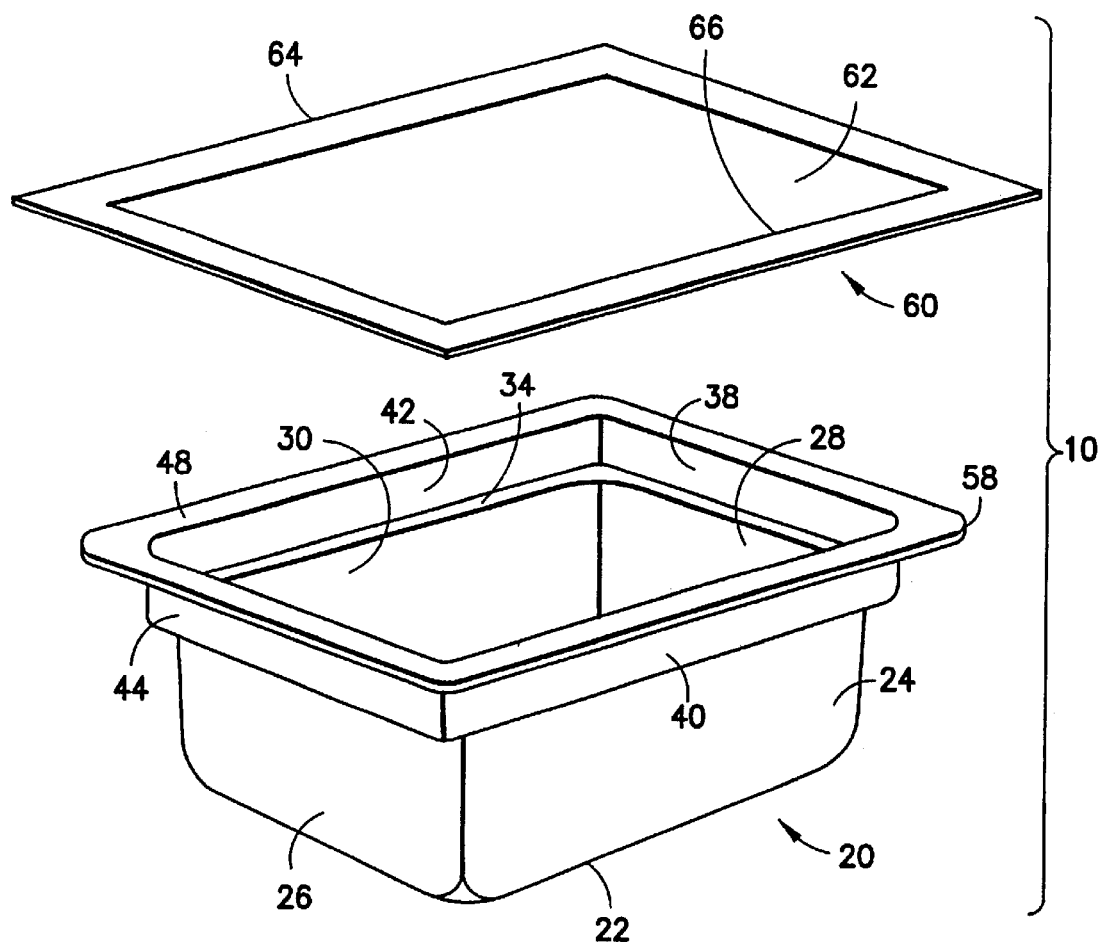
FIG. 1 is a perspective view of the medical device package of the present invention.
Figure 2:
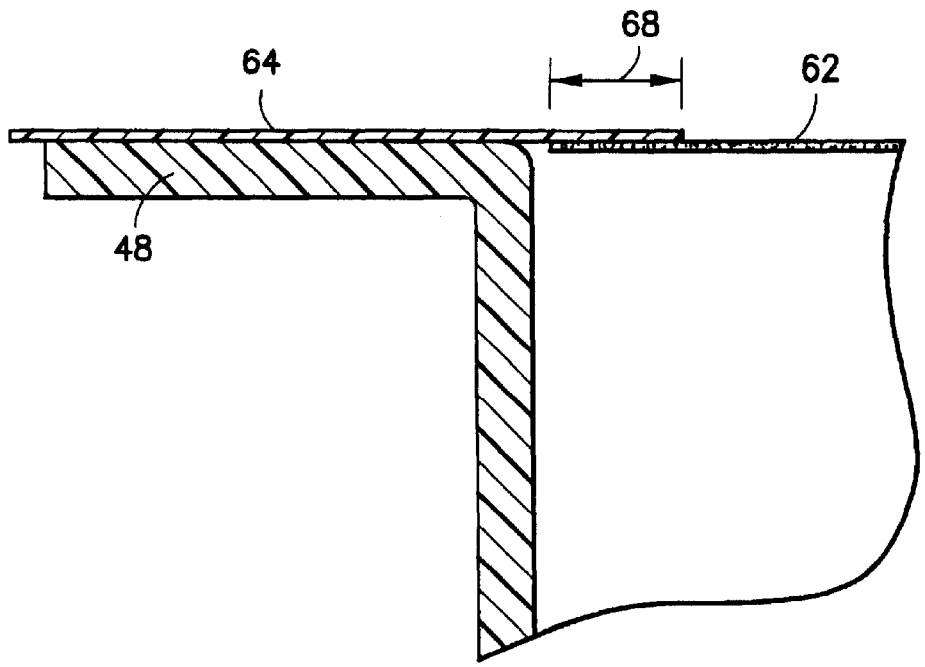
FIG. 2 is a sectional view of the medical device package of the present invention.
Figure 3:
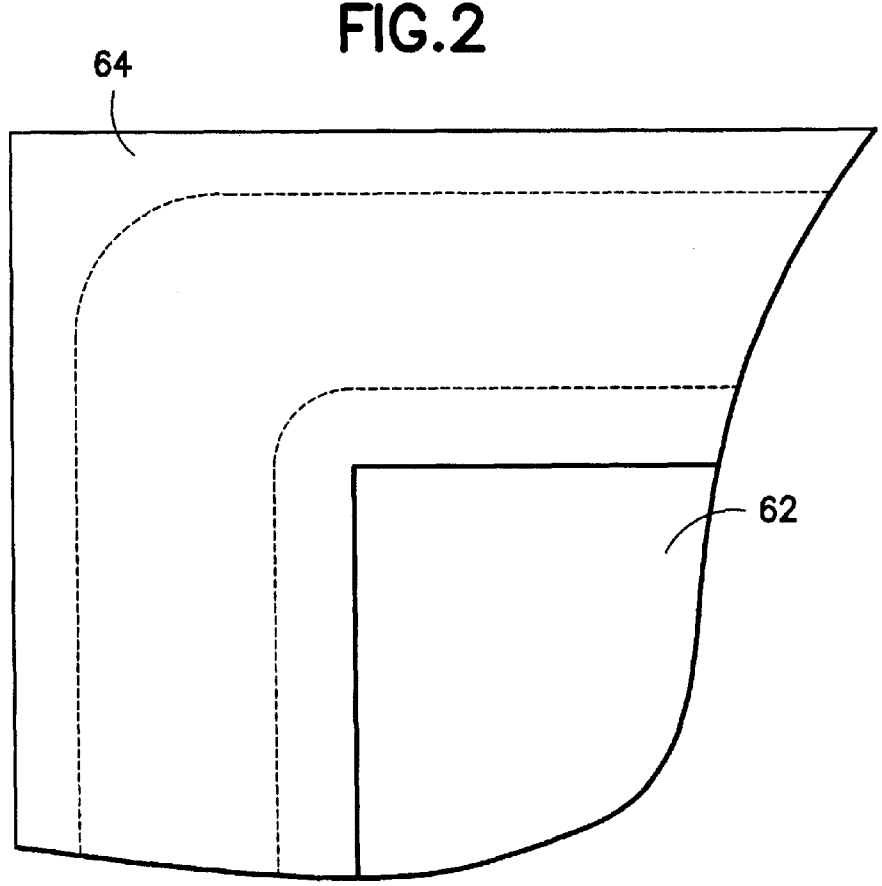
FIG. 3 is a plan view of a corner of the medical device package of the present invention.
Figure 4:
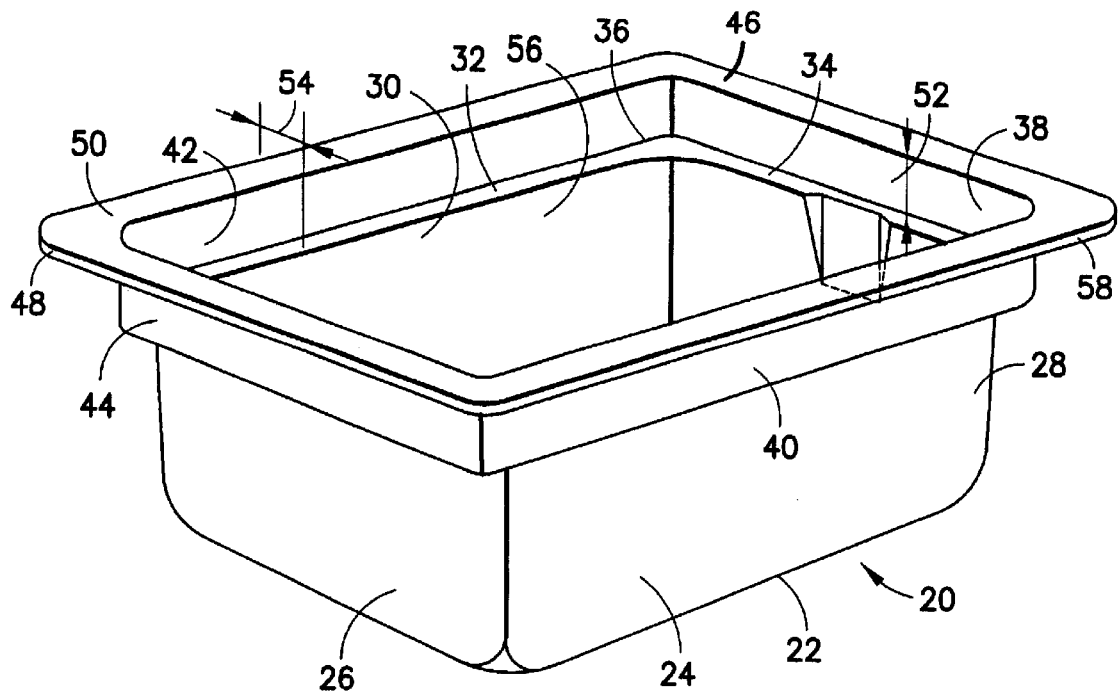
FIG. 4 is perspective view of the tub of the present invention.

There is shown generally in FIG. 1 at 10 the medical device package of the present invention. The medical device package 10 includes a tub 20 and a lid 60. With reference to FIGS. 1 and 4, the tub 20 has a planar base 22 from which four walls 24, 26, 28, 30 extend upward at approximately ninety degrees. The four walls 24, 26, 28, 30 terminate at an upper end 32 to form a first outwardly extending flange 34. The first flange intersects the upper end 32 of the walls at approximately ninety degrees and extends outwardly therefrom. There are four top walls 38, 40, 42, 44 extending upwardly at approximately ninety degrees from the outer edge 36 of the first outwardly extending flange 34. The four top walls 38, 40, 42, and 44 terminate at a second upper end 46 to form a second outwardly extending flange 48. The second outwardly extending flange 48 intersects the second upper end 46 at approximately ninety degrees and extends outwardly therefrom. The second outwardly extending flange has an upper surface 50 for mounting or adhering a lid 60 to the tub 20.

The gap 52 defined by the vertical distance between the first flange 34 and second flange 48 provides an area for use of an interior holding apparatus. Such an apparatus could hold the contents, for example syringes, and maintain the spatial arrangement of the contents of the package. The gap 52 also provides a depth for an automated opening tool to be utilized without contacting and possibly damaging the contents of the tub 20.

The horizontal or outward distance between the first flange 34 and second flange 48 defines a second gap 54. The contents of the tub 20 are contained inside the space 56 defined by the four walls 24, 26, 28, 30 and are inboard of the first flange 34. The gap 54, similar to the gap 52 defines a buffer zone when utilizing an automated opening tool such as a hot knife, or laser cutter to prevent damage of the contents of the tub 20.

The tub 20 is preferably formed of a plastic resin that allows the transmission of both visible and ultraviolet light. Examples of suitable materials for visible light transmission only, include high melt flow polycarbonate and high melt flow copolyester, which also exhibit good impact strength and overall durability. A particularly preferred resin of the present invention is methylpentene copolymer which transmits both visible and ultraviolet light and provides good mechanical protection of the contents of the tub. Specifically, the methylpentene copolymer demonstrates good transmissive properties at the microorganism killing ultraviolet wavelengths at 254 nanometers.

The tub 20 is preferably formed utilizing an injection molding process or a reaction injection molding process. In an injection molding process, the resin is injected into a mold under a specified temperature and pressure and allowed to cure to form a solid article.

Figure 5:
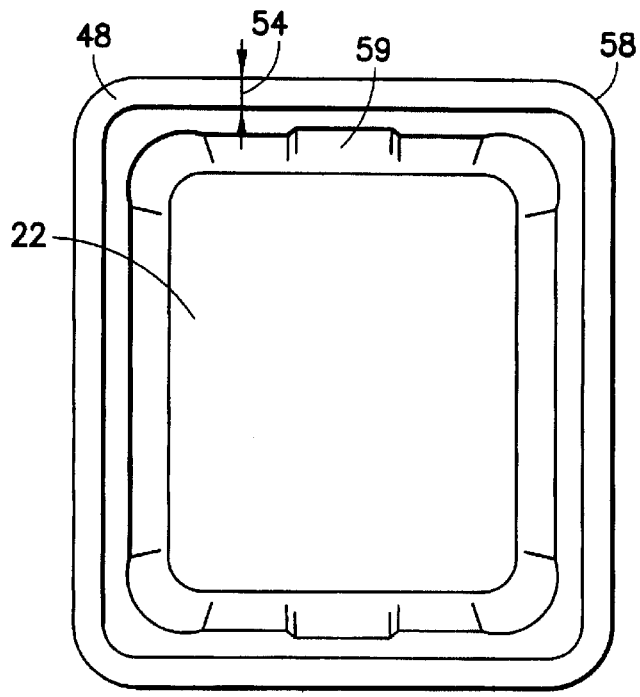
FIG. 5 is a plan view of the tub of the present invention showing the contours that facilitate release of the tub from a mold.

The tub 20 of the present invention, preferably, has radiused corners 58 both on its exterior and interior to facilitate removal of the tub 20 from the mold during manufacture. The radiused corners 58 also prevent the formation of sharp edges that may cause damage to the contents of the tub 20, as well as, pose a threat of possible injury to a person handling the tub 20. The tub 20 may also include contoured portions 59, as shown in FIGS. 4 and 5, to facilitate removal of the tub 20 from the mold during manufacture.

The lid 60 of the present invention comprises a gas permeable microfiber central portion 62 and a transparent plastic film 64 attached to the central portion 62 along its periphery 66.

The central portion 62 preferably comprises Tyvek®, a polyolefin microfiber material produced by E.I. Dupont de Nemours and Company of Wilmington, Del. Even more preferably, the central portion 62 comprises uncoated Tyvek® 1073B.

The transparent plastic film 64 is attached along the periphery 66 of the central portion using adhesives, glues or other bonding agents or may be heat welded. The transparent plastic film 64 should overlap 68 the central portion at least five millimeters to assure an adequate bonding between the two items.

The width of the transparent film 64 is variable, dependent upon the application to which it is to be associated. For example, if the lid 60 is to be removed manually utilizing a peel-away procedure, a narrow width in the range of 10–20 millimeters may be utilized. The 10–20 millimeter width would allow sufficient light to enter to sterilize the area just outside of the heat seal, but not be excessively wide from an economic perspective. If the lid 60 is to be utilized in an alternate application such as an automated opening operation, a wider width may be utilized to prevent possible shearing of the central portion 62, thereby producing particulate matter. A suitable width for the transparent film 64 is in the range of 20 to 30 millimeters for an automated procedure.

The film 64 should allow transmission of light in the ultraviolet spectrum for surface decontamination procedures. The film 64 should also have a sufficient shear strength to resist accidental tearing, but be capable of easy opening utilizing an automated system.

The present invention has been described in accordance with the relevant legal standards, thus the foregoing description is exemplary rather than limiting in nature. Variations and modifications to the disclosed embodiment may become apparent to those skilled in the art. Accordingly, the scope of legal protection afforded this invention can only be determined by studying the following claims.

What is claimed is:

1. A medical device package for containing a medical device, the package enabling sterilization of the medical device within the package and maintaining the medical device in a sterilized condition within the package, the package comprising:

a tub having a four-sided base and being formed of a clear, ultraviolet light transmitting plastic capable of withstanding exposure to steam and ethyleneoxide sterilization environments without degradation of said tub, the tub having four walls intersecting the base and extending upwardly therefrom and terminating at a first outwardly extending flange which extends laterally from the four walls; the first outwardly extending flange terminating at four top walls that extend from the first outwardly extending flange at approximately ninety degrees and terminating at a second outwardly extending flange that extends from the four top walls at approximately ninety degrees; and a lid removably fastenable to the tub and including a gas permeable central portion framed in a border of plastic film and in sealing engagement with the second flange; and wherein the medical device is sealable within the tub by the lid and wherein the tub enables sterilization of the medical device sealingly contained within the tub by the combined transmission of ultra violet light through the tub and of disinfectant gas through the lid.

2. The medical device package of claim 1, wherein the second outwardly extending flange extends outward a greater distance than the first outwardly extending flange.

3. The medical device package of claim 1, wherein a vertical distance from the first outwardly extending flange and the second outwardly extending flange defines a gap for use of an interior holding apparatus.

4. The medical device package of claim 1, where in a horizontal distance from the first outwardly extending flange and the second outwardly extending flange defining a second gap to provide a buffer zone when utilizing an automated opening procedure.

5. The medical device package of claim 1, wherein the tub is formed of high melt flow polycarbonate.

6. The medical device package of claim 1, wherein the tub is formed of high melt flow copolyester.

7. The medical device package of claim 1, wherein the tub is formed of methylpentene copolymer.

8. The medical device package of claim 1, wherein the tub further includes radiused corners to facilitate removal of the tub from a mold, and prevent the formation of sharp edges.

9. The medical device package of claim 1, wherein the tub further includes contoured portions to facilitate removal of the tub from a mold.

10. The medical device package of claim 1, wherein the tub is unitarily formed.

11. The medical device package of claim 1, wherein the tub comprises a plastic which transmits light at 254 nanometers for killing microorganisms.

12. The medical device package of claim 1, wherein the film is transparent.

13. The medical device package of claim 1, wherein the film and the central portion overlap.

14. The medical device package of claim 13, wherein the overlap is disposed inside of the four top walls.

* * * * *